US008491907B2

(12) United States Patent
Schreiber

(10) Patent No.: US 8,491,907 B2
(45) Date of Patent: Jul. 23, 2013

(54) **HUMAN ANTI-*PSEUDOMONAS-AERUGINOSA* IT-2 ANTIBODIES DERIVED FROM TRANSGENIC XENOMOUSE**

(75) Inventor: John R. Schreiber, Sudbury, MA (US)

(73) Assignee: Amgen, Inc., South San Francisco, CA (US)

( * ) Notice: Subject to any disclaimer, the term of this patent is extended or adjusted under 35 U.S.C. 154(b) by 0 days.

(21) Appl. No.: 12/835,179

(22) Filed: Jul. 13, 2010

(65) Prior Publication Data
US 2011/0177087 A1  Jul. 21, 2011

Related U.S. Application Data

(63) Continuation of application No. 10/581,564, filed as application No. PCT/US2004/040594 on Dec. 3, 2004, now abandoned.

(60) Provisional application No. 60/527,524, filed on Dec. 5, 2003.

(51) Int. Cl.
    *A61K 39/40* (2006.01)
(52) U.S. Cl.
    USPC ............... 424/170.1; 424/134.1; 424/164.1; 424/141.1; 424/150.1; 435/345; 435/366; 435/326; 435/328; 530/388.1; 530/388.15
(58) Field of Classification Search
    None
    See application file for complete search history.

(56) References Cited

FOREIGN PATENT DOCUMENTS

| EP | 0 441 395 A2 | 8/1991 |
|---|---|---|
| EP | 0 441 395 A3 | 10/1991 |
| WO | 96/33735 A1 | 10/1996 |
| WO | 02/20619 A2 | 3/2002 |
| WO | 03/040170 A2 | 5/2003 |
| WO | 03/048328 A2 | 6/2003 |

OTHER PUBLICATIONS

Rudikoff et al (Proc Natl Acad Sci USA 1982 vol. 79 p. 1979).*
MacCallum et al. J. Mol. Biol. (1996) 262,732-745.*
Pascalis et al. The Journal of Immunology (2002) 169, 3076-3084.*
Vajdos et al. (2002) 320, 415-428.*
Wu et al. J. Mol. Biol. (1999) 294, 151-162.*
Chen et al. J. Mol. Bio. (1999) 293, 865-881.*
Hemachandra et al., "Human Monoclonal Antibody (Mab) against *Pseudomonas aeruginosa* LPS Derived from Transgenic XenoMouse™ Mice Is Opsonic and Highly Protective in the Neutropenic Mouse Model of Sepsis," Clinical Infectious Diseases, (Jul. 2000), p. 213, vol. 31, No. 1, XP008005471, Chicago, IL, USA, abstract 10.
Hemachandra et al., "Human Monoclonal Antibodies against *Pseudomonas aeruginosa* Lipopolysaccharide Derived from Transgenic Mice Containing Megabase Human Immunoglobulin Loci Are Opsonic and Protective against Fatal *Pseudomonas* Sepsis," American Society for Microbiology, Infection and Immunity, (Apr. 2001), pp. 2223-2229, vol. 69, No. 4.

Lang et al., "Isolation and Characterization of a Human Monoclonal Antibody That Recognizes Epitopes Shared by *Pseudomonas aeruginosa* Immunotype 1, 3, 4, and 6 Lipopolysaccharides," American Society for Microbiology, Infection and Immunity, (Dec. 1989), pp. 3851-3855, vol. 57, No. 12.
Mendez et al., "Functional transplant of megabase human immunoglobulin loci recapitulates human antibody response in mice," Nature Genetics, (Feb. 15, 1997), pp. 146-156, vol. 15.
Preston et al., "Production and Characterization of a Set of Mouse-Human Chimeric Immunoglobulin G (IgG) Subclass and IgA Monoclonal Antibodies with Identical Variable Regions Specific for *Pseudomonas aeruginosa* Serogroup O6 Lipopolysaccharide," American Society for Microbiology, Infection and Immunity, (Sep. 1998), pp. 4137-4142, vol. 66, No. 9.
Sawada et al., "Immunoprotective Human Monoclonal Antibodies against Five Major Serotypes of *Pseudomonas aeruginosa*," Journal of General Microbiology, (1987), pp. 3581-3590, vol. 133.
Greenspan et al., "Defining epitopes: Its not as easy as it seems," Nature Biotechnology, (Oct. 1999), pp. 936-937, vol. 17.
Bowie et al., Deciphering the Message in Protein Sequences: Tolerance to Amino Acid Substitutions, American Association for the Advancement of Science, Science, (Mar. 16, 1990), pp. 1306-1310, vol. 247, No. 4948.
Hatano et al., "Immunogenic and Antigenic Properties of a Heptavalent High-Molecular-Weight O-Polysaccharide Vaccine Derived from *Pseudomonas aeruginosa*," American Society for Microbiology, Infection and Immunity, (Sep. 1994), pp. 3608-3616, vol. 62, No. 9.
Rudikoff et al., "Single amino acid substitution altering antigen-binding specificity," Proc. Natl. Acad. Sci. USA, Immunology, (Mar. 1982), pp. 1979-1983, vol. 79.
Zweerink et al., "Human Monoclonal Antibodies That Protect Mice against Challenge with *Pseudomonas aeruginosa*," American Society for Microbiology, Infection and Immunity, (Aug. 1988), pp. 1873-1879, vol. 56, No. 8.
Lai et al., "Multi-valent human monoclonal antibody preparation against *Pseudomonas aeruginosa* derived from transgenic mice containing human immunoglobulin loci is protective against fatal *pseudomonas* sepsis by multiple serotypes," Vaccine, Vo. 23, 2005, pp. 3264-3271, XP002341857.
Stanislavsky et al., "*Pseudomonas aeruginosa* antigens as potential vaccines," Federation of European Microbiological Societies, Published by Elsevier Science B.V., Oct. 10, 1997, pp. 243-277.
Hughes et al., "Synthetic Peptides Representing Epitopes of Outer Membrane Protein F of *Pseudomonas aeruginosa* That Elicit Antibodies Reactive with Whole Cells of Heterologous Immunotype Strains of *P. aeruginosa*," American Society for Microbiology, Infection and Immunity, vol. 60, No. 9, Sep. 1992, pp. 3497-3503.

* cited by examiner

*Primary Examiner* — Jennifer Graser
(74) *Attorney, Agent, or Firm* — Hahn Loeser & Parks LLP; John J. Cunniff

(57) ABSTRACT

The invention described herein provides for human antibodies produced in non-human animals that specifically bind to lipopolysaccharide (LPS) from strains Fisher Devlin (International Serogroups) It-2 (011), It-3 (02), It-4 (01), It-5 (010), It-6 (07), PA01 (05), 170003 (02), IATS016 (02/05), and 170006 (02). The invention further provides methods for making the antibodies in a non-human animal, expression of the antibodies in cell lines including hybridomas and recombinant host cell systems. Also provided are kits and pharmaceutical compositions comprising the antibodies and methods of treating or preventing pseudomonas infection by administering to a patient the pharmaceutical compositions described herein.

2 Claims, 3 Drawing Sheets

SEQUENCE LISTING

```
<160> NUMBER OF SEQ ID NOS: 30

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
cccaagcttt tcggcgaagt agtccttgac caggcagccc ag                          42

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcactcacta gtacatttgc gctcaac                                           27
```

```
<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gggaattcat ggactggacc tggaggrtyc tctkc                              35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gggaattcat ggagyttggg ctgasctggs tttyt                              35

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gggaattcat grammwactk tgkwscwysc tyctg                              35

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaggtrcagy tgctcgagtc tggrg                                         25

<210> SEQ ID NO 7
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagackcagy tgctcgagtc tgggrgc                                       27

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
caggtgcagc tgctcgagtc gggc                                          24
```

```
<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaggtgcagc tgctcgagtc tgg                                         23

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
caggwgcagc tgctcgagtc kggg                                        24

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
cccaagcttc atcagatggc gggaaga                                     27

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggaattcat ggacatgrrr dycchvgykc asctt                            35

<210> SEQ ID NO 13
<211> LENGTH: 120
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 13
```

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Pro Ala Gly Lys Gly Leu Glu Trp Ile
         35                  40                  45

Gly Arg Ile Tyr Thr Ser Gly Asn Thr Asn Tyr Lys Pro Ser Leu Lys
     50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
            85                  90                  95

Arg Glu Val Met Val Arg Gly Val Thr Phe Asp Tyr Trp Gly Gln Gly
        100                 105                 110

Thr Leu Val Thr Val Ser Ser Ala
        115                 120

<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 14

Gln Val Gln Leu Gln Glu Ser Gly Pro Gly Leu Val Lys Pro Ser Glu
  1               5                  10                  15

Thr Leu Ser Leu Thr Cys Thr Val Ser Gly Gly Ser Val Ser Asp Tyr
             20                  25                  30

Tyr Trp Ser Trp Ile Arg Gln Pro Pro Gly Lys Gly Leu Glu Trp Ile
         35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
             85                  90                  95

Arg Asp Gly Ser Val Pro Pro Gly Ile Tyr Trp Gly Gln Gly Thr Leu
        100                 105                 110

Val Thr Val Ser Ser Ala
        115

<210> SEQ ID NO 15
<211> LENGTH: 123
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 15

Gln Val Gln Leu Val Glu Ser Gly Gly Gly Val Val Gln Pro Gly Arg
  1               5                  10                  15

Ser Leu Arg Leu Ser Cys Ala Ala Ser Gly Phe Thr Phe Arg Tyr Gly
             20                  25                  30

Met His Trp Val Arg Gln Ala Pro Gly Lys Gly Leu Glu Trp Val Ala
         35                  40                  45

Val Ile Trp Tyr Asp Gly Asn Lys Lys Tyr His Ala Glu Ser Val Lys
     50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
             85                  90                  95

Arg Gly Gly Phe Gly Glu Leu Pro His Leu Tyr Gly Met Asp Val Trp
        100                 105                 110

Gly Gln Gly Thr Thr Val Thr Val Ser Ser Ala
        115                 120

```
<210> SEQ ID NO 16
<211> LENGTH: 122
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 16

Glu Val Gln Leu Val Glu Ser Gly Gly Gly Leu Val Lys Pro Gly Gly
 1               5                  10                  15

Ser Leu Arg Leu Ser Cys Ala Val Ser Gly Phe Thr Phe Ser Asn Ala
            20                  25                  30

Trp Met Ser Trp Val Arg Gln Thr Pro Gly Lys Gly Leu Glu Trp Val
        35                  40                  45

Gly Arg Ile Lys Ser Lys Thr Asp Gly Gly Thr Ile Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Lys Phe Tyr Tyr Gly Ser Gly Ser Tyr Gly Tyr Trp Gly
            100                 105                 110

Gln Gly Thr Leu Val Thr Val Ser Ser Ala
        115                 120

<210> SEQ ID NO 17
<211> LENGTH: 121
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 17

Gln Val Gln Leu Gln Gln Ser Gly Pro Gly Leu Val Lys Pro Ser Gln
 1               5                  10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
                85                  90                  95

Tyr Tyr Cys Ala Arg Gly Tyr Tyr Tyr Gly Met Asp Val Trp Gly Gln
            100                 105                 110

Gly Thr Thr Val Thr Val Ser Ser Ala
        115                 120

<210> SEQ ID NO 18
<211> LENGTH: 123
<212> TYPE: PRT
<213> ORGANISM: Artificial Sequence
<220> FEATURE:
<223> OTHER INFORMATION: Description of Artificial Sequence: Synthetic
      antibody
```

-continued

```
<400> SEQUENCE: 18

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr Tyr Tyr Tyr Asp Ser Ser Gly Tyr Tyr Tyr Tyr Trp
            100                 105                 110

Gly Gln Gly Thr Leu Val Thr Val Ser Ser Ala
        115                 120

<210> SEQ ID NO 19
<211> LENGTH: 122
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 19

Glu Val Gln Leu Val Gln Ser Gly Ala Glu Val Lys Lys Pro Gly Glu
1               5                   10                  15

Ser Leu Lys Ile Ser Cys Lys Gly Phe Gly Tyr Ser Phe Ala Ser Tyr
            20                  25                  30

Trp Ile Gly Trp Val Arg Gln Met Pro Gly Lys Gly Leu Glu Trp Met
        35                  40                  45

Gly Asn Ile Tyr Pro Gly Asp Ser Tyr Thr Ile Tyr Ser Pro Ser Phe
    50                  55                  60

Gln Gly Gln Val Ala Ile Ser Ala Asp Lys Ser Ile Ser Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Gly Phe Ser Gly Arg Ser Tyr Asp Ala Phe Glu Ile Trp
            100                 105                 110

Gly Gln Gly Thr Met Val Thr Val Leu Ala
        115                 120

<210> SEQ ID NO 20
<211> LENGTH: 125
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 20

Gln Val His Leu Gln Glu Ser Gly Pro Gly Leu Val Lys Pro Ser Glu
1               5                   10                  15

Thr Leu Ser Leu Thr Cys Thr Val Ser Gly Gly Ser Ile Thr Asn Phe
            20                  25                  30

Tyr Trp Ser Trp Ile Arg Gln Ser Ala Gly Lys Gly Leu Glu Trp Ile
        35                  40                  45
```

```
Gly Arg Ile Tyr Ile Ser Gly Thr Thr Asn Tyr Asn Pro Ser Leu Lys
        50                  55                  60

Ser Arg Val Thr Met Ser Leu Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg Gly Gly Tyr Ser Ile Gly Trp Tyr Arg Asp Leu Gly Ser Phe Asp
                100                 105                 110

Ile Trp Gly Gln Gly Thr Met Val Thr Val Ser Ser Ala
                115                 120                 125

<210> SEQ ID NO 21
<211> LENGTH: 117
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 21

Gln Val Gln Leu Gln Glu Ser Gly Pro Gly Leu Val Lys Pro Ser Glu
 1               5                   10                  15

Ser Leu Ser Leu Thr Cys Thr Val Ser Gly Gly Ser Val Ser Ser Tyr
                 20                  25                  30

Tyr Trp Ser Trp Ile Arg Gln Pro Ala Gly Lys Gly Leu Glu Trp Ile
             35                  40                  45

Gly Leu Ile Tyr Thr Ser Gly Ser Thr Asn Tyr Asn Pro Ser Leu Lys
        50                  55                  60

Ser Arg Val Thr Met Ser Val Asp Thr Ser Lys Asn Gln Phe Ser Leu
 65                  70                  75                  80

Lys Leu Ser Ser Val Thr Ala Ala Asp Ser Ala Val Tyr Tyr Cys Ala
                 85                  90                  95

Arg Ile Ala Ala Ala Gly Thr Asp Tyr Trp Gly Gln Gly Thr Leu Val
                100                 105                 110

Thr Val Ser Ser Ala
        115

<210> SEQ ID NO 22
<211> LENGTH: 113
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 22

Asp Ile Val Met Thr Gln Ser Pro Leu Ser Leu Pro Val Thr Pro Gly
 1               5                   10                  15

Glu Pro Ala Ser Ile Ser Cys Arg Ser Ser Gln Ser Leu Leu Phe Ser
                 20                  25                  30

Asn Glu Tyr Asn Phe Leu Asp Trp Phe Leu Gln Lys Pro Gly Gln Ser
             35                  40                  45

Pro Gln Leu Leu Ile Tyr Leu Gly Ser Asn Arg Ala Ser Gly Val Pro
        50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Met Gln Ala
                 85                  90                  95
```

```
Leu Gln Ile Pro Arg Thr Phe Gly Gln Gly Thr Lys Val Glu Ile Lys
                100                 105                 110

Arg

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 23

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Ile Arg Asn Val
                 20                  25                  30

Leu Val Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys Arg
                100                 105

<210> SEQ ID NO 24
<211> LENGTH: 114
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 24

Asp Ile Val Met Thr Gln Ser Pro Asp Ser Leu Ala Val Ser Leu Gly
  1               5                  10                  15

Glu Arg Ala Thr Ile Asn Cys Lys Ser Ser Gln Asn Ile Leu Tyr Asn
                 20                  25                  30

Ser Asn Asn Asn Asn Tyr Leu Ala Trp Phe Gln Gln Lys Pro Arg Gln
             35                  40                  45

Pro Pro Lys Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Asn Ser Leu Gln Ala Glu Asp Val Ala Val Tyr Tyr Cys Gln Gln
                 85                  90                  95

Tyr Tyr Ser Ala Pro Leu Thr Phe Gly Gly Gly Thr Lys Val Glu Ile
                100                 105                 110

Lys Arg

<210> SEQ ID NO 25
<211> LENGTH: 109
<212> TYPE: PRT
<213> ORGANISM: Artificial Sequence
<220> FEATURE:
<223> OTHER INFORMATION: Description of Artificial Sequence: Synthetic
      antibody
```

-continued

```
<400> SEQUENCE: 25

Glu Ile Val Leu Thr Gln Ser Pro Gly Thr Leu Ser Leu Ser Pro Gly
 1               5                  10                  15

Glu Arg Ala Thr Leu Ser Cys Arg Thr Ser Gln Ser Val Ser Ser Ile
             20                  25                  30

Tyr Leu Ala Trp Tyr Gln Gln Lys Pro Gly Gln Ala Pro Arg Leu Leu
         35                  40                  45

Ile Tyr Gly Ala Ser Asn Arg Ala Thr Gly Ile Pro Asp Arg Phe Ser
     50                  55                  60

Gly Ser Gly Phe Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Arg Ser Pro
                 85                  90                  95

Leu Thr Phe Gly Gly Gly Thr Lys Val Glu Ile Lys Arg
            100                 105

<210> SEQ ID NO 26
<211> LENGTH: 107
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 26

Glu Arg Val Met Thr Gln Ser Pro Ala Thr Leu Ser Val Ser Pro Gly
 1               5                  10                  15

Glu Arg Ala Thr Leu Ser Cys Arg Ala Ser Gln Ser Val Ser Ser Asn
             20                  25                  30

Leu Ala Trp Tyr Gln Gln Lys Pro Gly Gln Ala Pro Arg Leu Leu Ile
         35                  40                  45

Tyr Gly Ala Ser Thr Arg Ala Thr Gly Ile Pro Ala Arg Phe Ser Gly
     50                  55                  60

Ser Gly Ser Gly Thr Glu Phe Thr Leu Thr Ile Ser Ser Leu Gln Ser
 65                  70                  75                  80

Glu Asp Phe Ala Val Tyr Tyr Cys Gln Gln Tyr Tyr His Trp Leu Thr
                 85                  90                  95

Phe Gly Gly Gly Thr Lys Val Glu Ile Lys Arg
            100                 105

<210> SEQ ID NO 27
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 27

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Arg Asn Asp
             20                  25                  30

Leu Gly Trp Tyr Gln Gln Lys Pro Gly Lys Ala Pro Lys Arg Leu Ile
         35                  40                  45

Tyr Ala Ala Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80
```

```
Glu Asp Phe Ala Thr Tyr Tyr Cys Leu Gln Tyr Asn Ser Tyr Pro Pro
                85                  90                  95

Thr Phe Gly Gln Gly Thr Lys Val Glu Ile Lys Arg
            100                 105
```

<210> SEQ ID NO 28
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 28

```
Glu Ile Val Met Met Gln Ser Pro Gly Pro Leu Ser Val Ser Pro Gly
 1               5                  10                  15

Glu Arg Ala Ile Leu Ser Cys Arg Ala Ser Gln Asn Val Asn Ile Asn
                20                  25                  30

Leu Ala Trp Tyr Gln Gln Lys Pro Gly Gln Ala Pro Arg Leu Leu Ile
            35                  40                  45

Tyr Gly Ala Ser Thr Arg Ala Thr Gly Ile Pro Ala Arg Phe Ser Gly
50                  55                  60

Ser Gly Ser Gly Thr Glu Phe Thr Phe Thr Ile Ser Ser Leu Gln Ser
65                  70                  75                  80

Glu Asp Phe Ala Val Tyr Tyr Cys Gln Gln Tyr Lys Asn Trp Pro Leu
                85                  90                  95

Thr Phe Gly Gly Gly Thr Lys Val Glu Ile Lys Arg
            100                 105
```

<210> SEQ ID NO 29
<211> LENGTH: 113
<212> TYPE: PRT
<213> ORGANISM: Artificial Sequence
<220> FEATURE:
<223> OTHER INFORMATION: Description of Artificial Sequence: Synthetic
      antibody

<400> SEQUENCE: 29

```
Asp Ile Val Met Thr Gln Ser Pro Asp Ser Leu Ala Val Ser Leu Gly
 1               5                  10                  15

Glu Arg Ala Thr Ile Asn Cys Lys Ser Ser Gln Asn Ile Leu Tyr Ser
                20                  25                  30

Ser Asn Asn Lys Asn Tyr Leu Ala Trp Tyr Gln Gln Lys Pro Gly Gln
            35                  40                  45

Pro Pro Lys Leu Leu Ile Tyr Trp Ala Ser Thr Arg Glu Ser Gly Val
50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Phe Cys Gln Gln
                85                  90                  95

Tyr Tyr Asn Ile Arg Thr Phe Gly Gln Gly Thr Lys Val Glu Ile Lys
            100                 105                 110

Arg
```

<210> SEQ ID NO 30
<211> LENGTH: 108
<212> TYPE: PRT
<213> ORGANISM: Artificial Sequence
<220> FEATURE:
<223> OTHER INFORMATION: Description of Artificial Sequence: Synthetic
      antibody -continued

```
<400> SEQUENCE: 30

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Arg Asn Asp
             20                  25                  30

Leu Gly Trp Tyr Gln Gln Lys Pro Gly Lys Ala Pro Lys Arg Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln Tyr Lys Ser Tyr Pro Trp
                 85                  90                  95

Thr Phe Gly Gln Gly Thr Lys Val Glu Ile Lys Arg
                100                 105
```

HUMAN ANTI-*PSEUDOMONAS-AERUGINOSA* IT-2 ANTIBODIES DERIVED FROM TRANSGENIC XENOMOUSE

CROSS REFERENCE TO RELATED APPLICATIONS

This application is a continuation of U.S. application Ser. No. 10/581,564, filed Nov. 21, 2007 now abandoned, which is a United States National Stage Application under 35 U.S.C. §371 of International Application PCT/US2004/040594, filed Dec. 3, 2004, which claims priority to and the benefit of U.S. Provisional Application 60/527, 524 filed Dec. 5, 2003, now expired. The entire disclosures of each of the above applications is incorporated by reference herein.

TECHNICAL FIELD OF THE INVENTION

The present invention relates to compositions and methods for treating or preventing *Pseudomonas aeruginosa* infection and conditions caused by such infection. Specifically, the present invention relates to human antibodies that specifically bind to *P. aeruginosa* lipopolysaccharide (LPS) and nucleic acid molecules encoding them. The invention further relates to methods for making the antibodies in a non-human animal and expressing the antibodies in cell lines including hybridomas and recombinant host cell systems. The invention also relates to kits and pharmaceutical compositions comprising the antibodies. The invention further relates to methods of treating or preventing *P. aeruginosa* infection by administering to a patient any of the compositions described herein. The invention also relates to methods of detecting or diagnosing *P. aeruginosa* cells and/or infection.

BACKGROUND OF THE INVENTION

*P. aeruginosa* are Gram-negative, flagellated rod bacteria that continue to be a significant pathogen in nosocomial infections after surgery, prosthesis implantation and respiratory tract procedures. *P. aeruginosa* also is an opportunistic pathogen in the etiology of cancer, cystic fibrosis, diabetes, heart disease, otitis extema (swimmer's ear), osteomyelitis, corneal ulcers, folliculitis, mastitis, pneumonia, meningitis, urinary tract infections, endocarditis, peritonitis and other diseases found in geriatric or immunocompromised patients.

Surgical patients are often at increased risk of *P. aeruginosa* infection by virtue of their illness (e.g., trauma, burns, inhalation injury and cancer) or treatment (e.g., disruption of natural epithelial bathers by incision or percutaneous catheterization, endotracheal intubation, cardiac and thoracic surgery, neurosurgery, and gastrointestinal surgery). Disruption of natural intestinal flora by antibiotic treatments or prophylaxis, therapeutic immunosuppression of solid organ transplant recipients, or environmental exposure to *P. aeruginosa* can place patients at increased risk. Moreover, multi-drug-resistant strains can cause significant infections in inpatient units as well as nursing homes.

Surgical patients are affected by nosocomial pneumonia, often caused by *P. aeruginosa*. Onset occurs after the first 72 hours of hospitalization and is characterized by fever, purulent sputum, leukocytosis and a new or changed lung infiltrate revealed by chest radiography. The oropharynx is colonized rapidly, which may spread into the lower respiratory tract. Incidence of nosocomial infection in surgical patients overall is approximately 5% to 8%, and is probably higher in all critically ill patients. The incidence of pneumonia reported from surgical intensive care units (ICUs) is 15% to 20%, and occasionally higher. See Barie et al. *Am. J. Surgery* 179:2 S-7S (2000).

Cystic fibrosis (CF) patients suffer chronic colonization with a narrow but evolving spectrum of bacterial pathogens. *P. aeruginosa* remains the major CF pathogen with a worldwide prevalence of up to 80% to 90% in CF adults. Such infections lead to intermittent episodes of debilitating inflammatory exacerbations and progressive lung damage. Emerging pathogens also tend to be resistant to multiple antibiotic regimens. Thus, infection control plays a critical role in the quality of life and life expectancy of CF patients.

The onset of chronic colonization is associated with acceleration of forced expiratory volume (FEV). The original colonizing strain transforms into a mucoid colonial form which is due to copious production of a highly viscid exopolysaccharide known as alginate. The colonizing strain becomes significantly more mucinophilic and chemotactic and is associated with impaired mucociliary clearance. See Govan *J. Royal Soc. Med.* 93 Supp. 38:40-45 (2000). Moreover, the *P. aeruginosa* isolated from lungs of CF patients show changes in the LPS fatty acid acylation pattern and enhanced resistance to the bactericidal activity of some cationic antimicrobial peptides (CAMPs).

Alterations in *P. aeruginosa* LPS lipid A were found in CF isolates that increased both bacterial resistance to antimicrobial peptides and the ability of LPS to elicit inflammatory mediators. CF patients have very high antibody titers to *P. aeruginosa* LPS in both serum and sputum, which might neutralize its biological activities in vivo (e.g. proinflammatory mediator release). See Pier *Trends Microbial.* 8:247-251 (2000).

The leading cause of morbidity and mortality in severe burn wounds patients is infection with *P. aeruginosa*. See Lee et al. *Vaccine* 18:1952-1961 (2000). Burn wounds are highly exudative, creating a moist, nutrient-rich environment for bacterial colonization. Burn wounds are largely inaccessible to the patient's immune responses and vascularly delivered antibiotics, due to the severe tissue injury. Moreover, burn wounds leave the host immunocompromised with endogenously decreased levels of immunoglobulin gamma (IgG). Without treatment, burn wound infections can spread and develop into sepsis with the associated production of inflammatory cytokines, including interleukin-1 (IL-1), IL-6, and tumor necrosis factors (TNFs). Burn wound infections may also result in delayed healing, increased scarring, conversion of a partial thickness defect to a full thickness defect and increased nutritional demands. Intravenous immunoglobulin (IVIG) has been used increasingly to treat both bacterial and viral infections and primary and secondary immunodeficiency disorders. IVIG is comprised of pooled human polyclonal antibodies from normal donors which are used as a substitution therapy for primary and secondary antibody deficiencies and to treat immune-mediated diseases, including autoimmune and systemic inflammatory conditions. Immunoglobulins promote the opsonization and phagocytosis of bacteria, neutralization of bacterial toxins, inhibition of microbial attachment, and the complement-induced lysis of bacteria. See Felts et al. *Burns* 25:415-423 (1999).

Direct and local delivery of protective immunoglobulins to wound and burn sites represents a rational means to overcome the lack of vascularization of burn wounds as well as biofilm barriers. Local delivery of IgG, both prophylactically and post-infection, was demonstrated to improve survival in mouse models of *P. aeruginosa* infected burn wounds. See Felts et al. *Burns* 25:415-423 (1999).

Advances in the bioengineering of prosthetic devices has improved the lives of millions of patients. However, this progress has been tempered by implant-associated infections that often resist antibiotic treatment. Infectious organisms, including *P. aeruginosa*, preferentially target synthetic implanted materials, eliciting serious and costly infections that frequently require removal of the colonized device.

Initial microbial adhesion is a primary determinant of biomaterial colonization because initially adhering microorganisms often progress to a mature biofilm attached to the biomaterial surface. The focus of research aimed at reducing biofilm formation on prostheses has been directed toward modifying or coating the surface of the implanted materials. Approaches utilizing surface chemistry and antibiotic-releasing coatings, however, have not been fully successful.

Because surgical sites are often immunocompromised, a promising approach involves the immunostimulation of the local wound site. Studies have shown that pooled polyclonal human antibodies opsonize infecting bacteria, and pooled antibodies can inhibit *P. aeruginosa* adhesion rates and surface-growth dynamics, thus reducing biofilm formation. See Poelstra et al. *J. Biomed. Mat. Res.* 51:224-232 (2000).

Peritonitis is often caused by ulcers, appendicitis, diverticulitis, ileus, gunshot or stab wounds, disturbances during abdominal surgery, and continuous ambulatory peritoneal dialysis (CAPD). Nosocomial peritonitis, caused by exogenous pathogenic bacteria including *P. aeruginosa*, is an especially acute problem for immunocompromised and geriatric populations.

Current treatment regimens for peritonitis focus on antibiotics. However, antibiotic resistance occurs at a significant rate and is frequently associated with clinical failure. IVIG has shown promising but inconsistent results in peritonitis, however, as with burn wounds, local (peritoneal) delivery of pooled polyclonal immunoglobulin against *P. aeruginosa* was shown to significantly reduce infection in a mouse model. See Barekzi et al. *Antimicrob. Agents Chemotherap.* 43:1609-1615 (1999).

Treating *P. aeruginosa* infections with antibiotic regimens has become increasingly difficult because, inter alia, antibiotic resistant strains have arisen.

Non-human antibody preparations, including murine monoclonal antibodies, are not generally acceptable for human therapies because of their immunogenicity. Human polyclonal antibody preparations, although suitable for human therapies, have variable titers of protective antibodies for *P. aeruginosa* and a high cost of purifying antibodies from multiple donors.

Human IgM monoclonal antibodies penetrate poorly into pulmonary tissue and can be associated with immune complex formation and enhanced inflammation.

We previously described the use of immunoglobulin-inactivated mice that have been reconstituted with megabase-size contiguous fragments of human immunoglobulin loci via yeast artificial chromosomes to make entirely human monoclonal antibodies against *P. aeruginosa*. We made an IgG2 Mab against the polysaccharide (PS) portion of the LPS O-specific side chain of International Serogroup Type 06ad (Fisher Devlin It-1) *P. aeruginosa*. See U.S. Pat. No. 7,972, 845, issued Jul. 5, 2011, which is incorporated herein by reference in its entirety. This human Mab has strong avidity for 06ad O-side chain PS, is opsonic for uptake and killing of the bacteria by human polymorphonuclear leukocytes (PMN), and is highly protective in preventing mortality in the neutropenic mouse model of pseudomonas sepsis. However, *P. aeruginosa* is classified into 20 serogroups based on O-specific side chains and this monoclonal antibody is highly specific for 06ad *P. aeruginosa*. Therefore, this antibody is not effective against other *P. aeruginosa* serogroups.

Therefore, there remains a need for additional therapeutically useful antibodies to treat or prevent infection with other common *P. aeruginosa*, especially against other serogroups and corresponding multivalent compositions, methods for their preparation and use, and pharmaceutical compositions and kits comprising them.

SUMMARY OF THE INVENTION

The present invention provides isolated antibodies, particularly human antibodies, that specifically bind to *P. aeruginosa* lipopolysaccharide (LPS) from various strains of *P. aeruginosa* and combinations of the antibodies. The invention further provides methods for making the antibodies in a non-human animal, expression of the antibodies in cell lines including hybridomas and recombinant host cell systems. The invention also provides kits and pharmaceutical compositions comprising the antibodies. In addition, the invention provides methods of treating or preventing pseudomonas infection by administering to a patient the pharmaceutical compositions described herein. The invention also provides methods of detecting or diagnosing *P. aeruginosa* cells and/or infection.

DETAILED DESCRIPTION OF THE INVENTION

Figure 1:
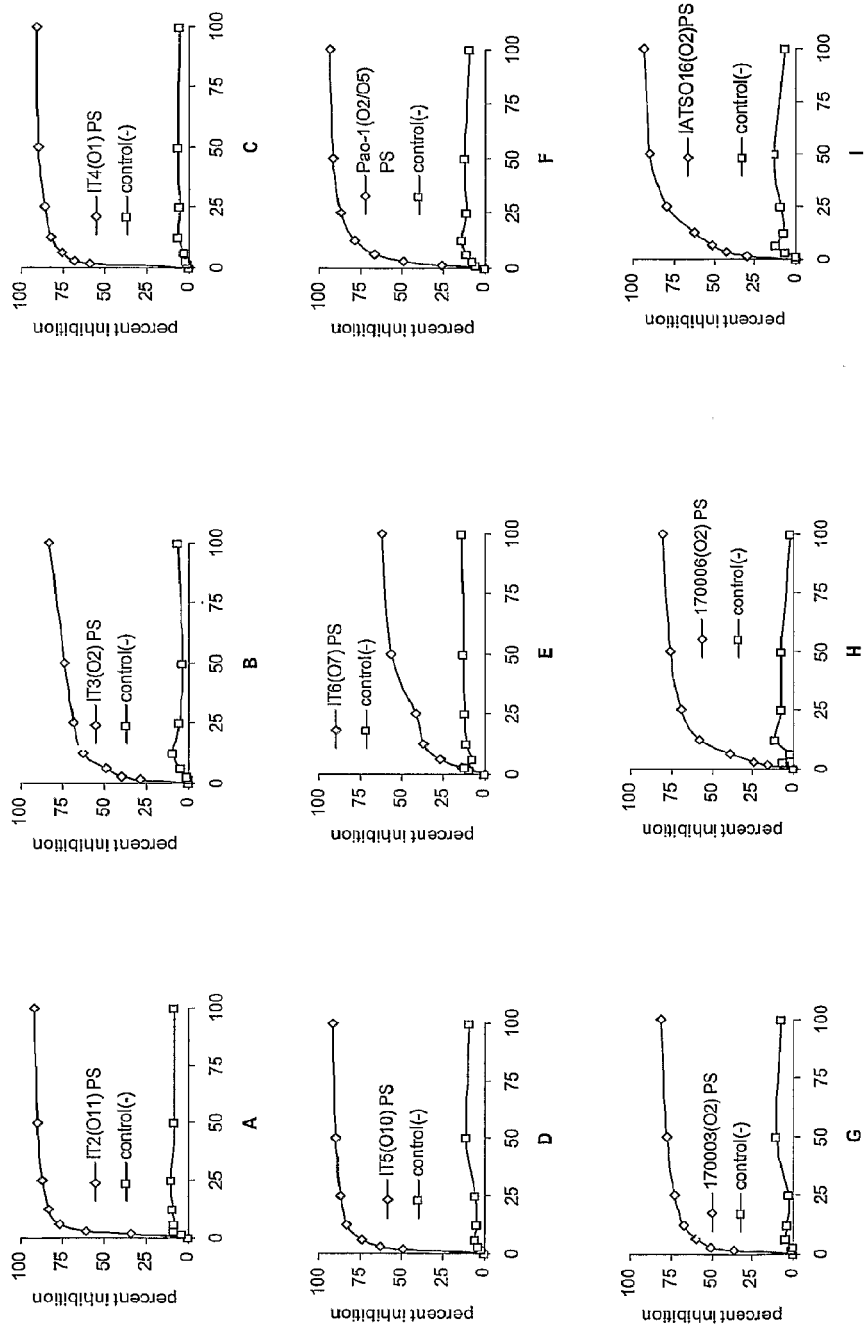
FIG. 1 shows blocking of ten serogroup-specific human Mabs to *P. aeruginosa* immobilized on an ELISA plate by the corresponding purified O-side chain polysaccharide ("PS"; diamonds) but not by control PS of a different subgroup (squares).

The invention provides isolated antibodies or antigen-binding portions thereof that specifically bind to *P. aeruginosa* LPS from strains Fisher Devlin (International Serogroups) It-2 (011), It-3 (02), It-4 (01), It-5 (010), It-6 (07), PA01 (05), 170003 (02), IATS016 (02/05), or 170006 (02). In some embodiments, the antibodies specifically bind to *P. aeruginosa* LPS from more than one strain as follows: It-3 (02) and IATS016 (02/05); or PA01 (05) and 170006 (02). In a preferred embodiment, the antibodies are fully human. In some embodiments, the antibodies are monoclonal. In other aspects, the invention provides the amino acid sequences of the antibodies' heavy and light chains or the variable domains thereof or portions of the variable domains, in particular sequences corresponding to a contiguous heavy and light chain sequences from CDR1 through CDR3 and to the heavy and light chain CDRs. The invention further provides nucleic acid molecules encoding said antibody chains and portions. Further provided are antibodies having similar binding properties and antibodies (or other antagonists) having similar functionality as antibodies disclosed herein. Hybridomas expressing such immunoglobulin molecules and monoclonal antibodies are also provided.

The terms herein generally have their usual meaning as understood by those of ordinary skill in the art. The following terms are intended to have the following general meanings as they are used herein:

"B lymphocytic cells or progeny thereof" refer to any cell descending from, to or destined for, the B lymphocytic lineage. Examples include, but are not limited to, all B lymphocytes in the B cell developmental pathway starting from the earliest B lymphocyte stem cells through memory B cells, plasma cells, and any hybridomas created in vitro.

"Bispecific antibodies" are single antibodies that have affinities for two separate antigens. For example, a bispecific antibody might recognize *P. aeruginosa* LPS using one combination of heavy and light chains and might recognize a leukocyte cell surface marker using a second combination of heavy and light chains attached to the first combination. See McCormick et al. *J. Immunol.* 158:3474-3482 (1997).

"Chimeric antibodies" are antibodies that have been altered from their original form to comprise amino acid sequences from another antibody or from a non-antibody protein. Chimeric antibodies retain at least a portion of the original antibody amino acid sequence, typically the portion comprising the antigen binding region. Examples of chimeric antibodies include, but are not limited to, bispecific antibodies and fusions with other non-immunoglobulin protein sequences.

"Cytokines" refer generally to signaling molecules of the immune system. Cytokines include, but are not limited to, Interleukins (IL), transforming growth factors (TGF), tumor necrosis factors (TNF), lymphotoxins (LT), interferons, granulocyte-macrophage colony stimulating factors (GM-CSF), macrophage CSF, granulocyte CSF, and migration inhibition factors.

"Derivatize" refers to the process of attaching a non-immunoglobulin agent to the immunoglobulin molecules. Examples of derivatizing agents include, but are not limited to, toxins, complement, antibiotics, peptides, polysaccharides, lipids, organic polymers, radiolabels, and inorganic compounds.

"Expression control sequences" refer to sequences that allow for the inducible or constitutive expression of gene sequences under specific conditions or in specific cells. Examples of cellular processes that expression control sequence regulate include, but are not limited to, gene transcription, protein translation, messenger RNA splicing, immunoglobulin isotype switching, protein glycosylation, protein cleavage, protein secretion, intracellular protein localization and extracellular protein homing.

"Fusion Proteins" refer to chimeric proteins comprising amino acid sequences of two or more different proteins. Typically, fusion proteins result from in vitro recombinatory techniques well known in the art. However, fusion proteins may result from in vivo crossover or other recombinatory events.

"Human immunoglobulin molecules" refer to immunoglobulin proteins that utilize human immunoglobulin gene sequences. The immunoglobulin gene sequences may be expressed in any non-human animal.

"Human monoclonal antibodies" refer to antibodies that are members of a population of human antibodies with identical specificities. The population of human antibodies may be produced in a hybridoma or other immortalized cell line as well as in recombinant cell lines expressing the exogenous human antibody gene sequences.

"Immunocompromised patients" refer to patients whose immune responses to foreign antigens or agents is impaired either by disease (e.g. AIDS), by invasive surgery, or by drug therapies in connection with treatments for other conditions (e.g. organ transplant patients).

"Label" refers to any molecule that attaches to the claimed immunoglobulin a functional characteristic not normally associated with that immunoglobulin. Labels can be attached via chemical modification of the immunoglobulin, recognition of the label by one of the two Fab regions of a bispecific immunoglobulin, affinity for a third agent (e.g. the avidin/biogen interaction), radiolabeling, or as a fusion protein expressed recombinantly. Labels can function as molecular or radioactive tags for clinical or research purposes or as agents for combating *P. aeruginosa* infection (e.g. toxins or complement proteins). Other examples of labels can include enzymes, fluorescent molecules, magnetic labels, epitope tags (e.g. *H. influenza* hemaglutinin), antibiotics, complement proteins, and cytokines.

"Respiratory patients" refer to any patient that is either being treated for a disease of the respiratory system or is receiving respiratory care, e.g. intubation or ventilation, in connection with some other medical treatment.

"Surgical patients" refer to any patient that is subject to an invasive surgical procedure, typically involving puncturing or incising the dermis.

"Toxins" refer to protein or non-protein compounds that can be attached to antibodies for the purpose of killing the cells to which the antibodies have attached. Examples of toxins include, but are not limited to, complement, antibiotics, peptides, polysaccharides, lipids, organic polymers, radiolabels, and inorganic compounds.

"Vectors" refer to DNA or RNA molecules that allow sequences of interest to be cloned, propagated, recombined, mutated, or expressed outside of their native cells. Often vectors have expression control sequences that allow for the inducible or constitutive expression of gene sequences under specific conditions or in specific cells. Examples of vectors include, but are not limited to, plasmids, yeast artificial chromosomes (YACs), viruses, bacteriophages, and phagemids.

"XenoMouse™" refers to mice bearing inactivated endogenous immunoglobulin loci, rendering them incapable of expressing endogenous murine immunoglobulin, but bearing substantial portions of human immunoglobulin loci. Mice of the XenoMouse™ line are capable of somatic rearrangement of the human immunoglobulin genes, hypermutation of the human variable genes, and immunoglobulin isotype switching. Therefore, the mice of the XenoMouse™ line are capable of mounting effective humoral responses to antigenic challenge utilizing the human immunoglobulin gene sequences. The resulting antibodies are fully human and can be isolated from the animals themselves, from cultured cells extracted from the animals, and from hybridomas created from XenoMouse™ B lymphocytic lines or progeny thereof. Moreover, the rearranged human gene sequences encoding immunoglobulins raised against specific antigenic challenges can be isolated by recombinant means well known in the art.

Antibody Structure

The basic antibody structural unit comprises a tetramer, composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as kappa and lambda light chains. Heavy chains are classified as mu, delta, gamma, alpha, and epsilon, and define the antibody's isotype as IgM, IgD, IgG, IgA, and IgE, respectively. Within light and heavy chains, the variable and constant regions are joined by a "J" region of about 12 or more amino acids, with the heavy chain also including a "D" region of about 10 more amino acids. See generally, *Fundamental Immunology* Ch. 7 (Paul, W., ed., 2nd ed. Raven Press, N.Y. (1989)) (incorporated by reference in its entirety for all purposes). The variable regions of each light/heavy chain pair form the antibody binding site. Thus, an intact IgG antibody has two binding sites. Except in bifunctional or bispecific antibodies (discussed below), the two binding sites are the same.

The chains all exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminal to C-terminal, both light and heavy chains comprise the domains FR1, CDR1, FR2, CDR2, FR3, CDR3 and FR4. The assignment of amino acids to each domain is in accordance with the definitions of Kabat *Sequences of Proteins of Immunological Interest* (National Institutes of Health, Bethesda, Md. (1987 and 1991)), or Chothia & Lesk *J. Mol. Biol.* 196:901-917 (1987); Chothia et al. *Nature* 342:878-883 (1989).

A bifunctional or bispecific antibody is an artificial hybrid antibody having two different heavy/light chain pairs and two different binding sites. Bispecific antibodies can be produced by a variety of methods including fusion of hybridomas or linking of Fab' fragments. See, e.g., Songsivilai & Lachmann *Clin. Exp. Immunol.* 79:315-321 (1990), Kostelny et al. *J. Immunol.* 148:1547-1553 (1992). In addition, bispecific antibodies may be formed as "diabodies" (Holliger et al. "'Diabodies': small bivalent and bispecific antibody fragments" *Proc. Natl. Acad. Sci. USA* 90:6444-6448 (1993)) or "Janusins" (Traunecker et al. "Bispecific single chain molecules (Janusins) target cytotoxic lymphocytes on HIV infected cells" *EMBO J.* 10:3655-3659 (1991) and Traunecker et al. "Janusin: new molecular design for bispecific reagents" *Int. J. Cancer Suppl.* 7:51-52 (1992)). Production of bispecific antibodies can be a relatively labor intensive process compared with production of conventional antibodies and yields and degree of purity are generally lower for bispecific antibodies. Bispecific antibodies do not exist in the form of fragments having a single binding site (e.g., Fab, Fab', and Fv).

Human Antibodies from Non-Human Animals

Human antibodies avoid certain of the problems associated with antibodies that possess murine or rat variable and/or constant regions. The presence of such murine or rat-derived proteins can lead to the rapid clearance of the antibodies or can lead to the generation of an immune response against the antibody by a human patient. In order to avoid the utilization of murine or rat-derived antibodies, it has been postulated that one can develop humanized antibodies or generate fully human antibodies through the introduction of human antibody function into a rodent so that the rodent would produce fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the utilization of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (Mabs)—an important milestone towards fulfilling the promise of antibody therapy in human disease. Fully human antibodies are expected to minimize the immunogenic and allergic responses intrinsic to mouse or mouse-derivatized Mabs and thus to increase the efficacy and safety of the administered antibodies. The use of fully human antibodies can be expected to provide a substantial advantage in the treatment of chronic and recurring human diseases, such as inflammation, autoimmunity, cancer and bacterial infections, which potentially require repeated antibody administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human Mabs with the desired specificity could be readily produced and selected.

This general strategy was demonstrated in connection with the generation of the first XenoMouse™ strains as published in 1994. See Green et al. *Nature Genetics* 7:13-21 (1994). The XenoMouse™ strains were engineered with yeast artificial chromosomes (YACs) containing 245 kb- and 190 kb-sized germline configuration fragments of the human heavy chain locus and kappa light chain locus, respectively, which contained core variable and constant region sequences. Id. The human Ig containing YACs proved to be compatible with the mouse system for both rearrangement and expression of antibodies and were capable of substituting for the inactivated mouse Ig genes. This was demonstrated by their ability to induce B-cell development, to produce an adult-like human repertoire of fully human antibodies, and to generate antigen-specific human Mabs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively, to produce XenoMouse™ mice. See Mendez et al. *Nature Genet.* 15:146-156 (1997), Green and Jakobovits *J. Exp. Med.* 188:483-495 (1998), and U.S. patent application Ser. No. 08/759,620, filed Dec. 3, 1996, the disclosures of which are hereby incorporated by reference.

Such an approach is further discussed and delineated in U.S. patent application Ser. No. 08/031,801, filed Mar. 15, 1993 (now U.S. Pat. No. 6,673,986). See also Mendez et al.

Nature Genet. 15:146-156 (1997) and Green and Jakobovits J. Exp. Med. 188:483-495 (1998). See also U.S. Pat. Nos. 5,916,771, 5,939,598, 5,985,615, 5,998,209, 6,075,181, 6,091,001, 6,114,598, 6,130,364, 6,162,963 and 6,150,584. See also U.S. Pat. Nos. 6,657,103 and 6,713,610 and U.S. Pat. Pub. Nos. 2003/229905, 2004/010810, 2004/093622, 2005/054055, 2005/076395, 2006/040363, 2010/010202, U.S. Pat. Pub. Nos. 2005/241006, 2005/287630, 2009/149637, 2012/117669, U.S. Pat. Nos. 6,207,418, and 6,420,140 and U.S. Pat. Pub. Nos. 2002/076763, 2004/142430, 2003/022291, U.S. Pat. Pub. Nos. 2003/070185, 2008/235814, 2008/098490, U.S. Pat. No. 6,235,883 and U.S. Pat. Pub. Nos. 2006/183887, 2002/173629, 2005/100546, 2010/305307, U.S. Pat. Pub. Nos. 2006/104974, 2007/048305, U.S. Pat. Pub. Nos. 2002/029391 and 2003/092125, U.S. Pat. Pub. No. 2002/142374, U.S. Pat. No. 6,682,736 and U.S. Pat. Pub. Nos. 2004/228858, 2004/228861, 2005/287136, 2008/233116, 2008/233122, 2012/045442. The disclosures of each of the above-cited U.S. patents and published U.S. applications are hereby incorporated by reference in their entirety.

Antibodies in accordance with the present invention are preferably prepared through the utilization of a transgenic mouse that has a substantial portion of the human antibody producing genome inserted but that is rendered deficient in the production of endogenous, murine antibodies. Such mice, then, are capable of producing human immunoglobulin molecules and antibodies and are deficient in the production of murine immunoglobulin molecules and antibodies. Technologies utilized for achieving the same are disclosed in the patents, applications, and references disclosed herein.

Through use of such technology, fully human monoclonal antibodies, or the antigen binding portions thereof, to *P. aeruginosa* LPS were produced. Essentially, we immunized XenoMouse™ lines of mice with heat-killed *P. aeruginosa*, recovered spleen and lymph node cells (such as B-cells) from the mice that express *P. aeruginosa* LPS antibodies, fused such recovered cells with nonsecreting myeloma cells to prepare immortal hybridoma cell lines, and screened hybridoma cell lines to identify those that produce antibodies specific to the antigen of interest.

As will be appreciated, antibodies in accordance with the present invention can be expressed in cell lines other than hybridoma cell lines. Sequences encoding particular antibodies can be used for transformation of a suitable host cell. Transformation can be by any known method for introducing polynucleotides into a host cell, including, for example, packaging the polynucleotide in a virus (or into a viral vector) and transducing a host cell with the virus (or vector) or by transfection procedures known in the art, as exemplified by U.S. Pat. Nos. 4,399,216, 4,912,040, 4,740,461, and 4,959,455 (which patents are hereby incorporated herein by reference). The transformation procedure used depends upon the host to be transformed. Methods for introduction of heterologous polynucleotides into mammalian cells are well known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are well known in the art and include many immortalized cell lines available from the American Type Culture Collection (ATCC), including but not limited to Chinese hamster ovary (CHO) cells, NS/O, HeLa cells, baby hamster kidney (BHK) cells, monkey kidney cells (COS), human hepatocellular carcinoma cells (e.g., Hep G2), and a number of other cell lines. Cell lines of particular preference are selected through determining which cell lines have high expression levels and produce antibodies with constitutive *P. aeruginosa* LPS binding properties.

Further, expression of antibodies of the invention (or other moieties therefrom) from production cell lines can be enhanced using a number of known techniques. For example, enhanced expression can be realized by the coamplification expression system utilizing dihydrofolate reductase (DHFR) or the glutamine synthetase gene expression system (the GS system). See, e.g. Kaufman and Sharp *J. Mol. Biol.* 159:601-621 (1982); European Patent Nos. 0 216 846, 0 256 055, and 0 323 997; and European Patent Application No. 89303964.4.

Antibodies of the invention also can be produced through the generation of a mammal or plant that is transgenic for the immunoglobulin heavy and light chain sequences of interest and production of the antibody in a recoverable form therefrom. In connection with the transgenic production in mammals, antibodies can be produced in, and recovered from, the milk of goats, cows, or other mammals. See, e.g., U.S. Pat. Nos. 5,827,690, 5,756,687, 5,750,172, and 5,741,957.

The invention provides an isolated human antibody or antigen-binding portion thereof that was expressed in a non-human animal and specifically binds to the LPS from one of *P. aeruginosa* strains Fisher Devlin (International Serogroups) It-2 (011), It-3 (02), It-4 (01), It-5 (010), It-6 (07), PA01 (05), 170003 (02), IATS016 (02/05), and 170006 (02). In a preferred embodiment, the isolated human antibody or antigen-binding portion thereof is a monoclonal antibody.

The invention further provides the isolated human antibody or antigen-binding portion thereof that is opsonic for *P. aeruginosa* cells from one of strains Fisher Devlin (International Serogroups) It-2 (011), It-3 (02), It-4 (01), It-5 (010), It-6 (07), PA01 (05), 170003 (02), IATS016 (02/05), and 170006 (02). In a preferred embodiment, the isolated human antibody or antigen-binding portion thereof facilitates phagocytosis of the *P. aeruginosa* cells.

The invention also provides that the isolated human antibody or antigen-binding portion thereof enhances the immune response to *P. aeruginosa* from one of strains Fisher Devlin (International Serogroups) It-2 (011), It-3 (02), It-4 (01), It-5 (010), It-6 (07), PA01 (05), 170003 (02), IATS016 (02/05), and 170006 (02). In a preferred embodiment, the isolated human antibody or antigen-binding portion thereof facilitates the killing of *P. aeruginosa* cells. In a more preferred embodiment, the isolated human antibody or antigen-binding portion thereof facilitates the killing of *P. aeruginosa* cells by delivering an agent that is lethal to the *P. aeruginosa* cells.

The invention provides an isolated human antibody or antigen-binding portion thereof that specifically binds to LPS from one of *P. aeruginosa* strains Fisher Devlin (International Serogroups) It-2 (011), It-3 (02), It-4 (01), It-5 (010), It-6 (07), PA01 (05), 170003 (02), IATS016 (02/05), and 170006 (02), wherein the antibody or antigen-binding portion thereof inhibits *P. aeruginosa* infection.

The invention also provides a human anti-*P. aeruginosa* LPS antibody that binds the same antigen or epitope as a human anti-*P. aeruginosa* LPS antibody provided herein. Further, the invention provides a human anti-*P. aeruginosa* LPS antibody that competes or cross-competes with a human anti-*P. aeruginosa* LPS antibody of the invention. One may determine whether an anti-*P. aeruginosa* LPS antibody binds to the same antigen as another anti-*P. aeruginosa* LPS antibody using a variety of methods known in the art. For instance, one can use a known anti-*P. aeruginosa* LPS antibody to capture the antigen, elute the antigen from the anti-*P. aeruginosa* LPS antibody, and then determine whether the test antibody will bind to the eluted antigen. One may determine whether an antibody competes with an anti-*P. aeruginosa* LPS antibody by binding the antibody to *P. aeruginosa* or LPS under saturating conditions, and then measuring the ability of the test antibody to bind to *P. aeruginosa* or LPS. If the test antibody is able to bind to the *P. aeruginosa* or LPS at the same time as the anti-*P. aeruginosa* LPS antibody, then the test antibody binds to a different epitope than the anti-*P. aeruginosa* LPS antibody. However, if the test antibody is not able to bind to the *P. aeruginosa* or LPS at the same time, then the test antibody competes with the human anti-*P. aeruginosa* LPS antibody. This experiment may be performed using ELISA or surface plasmon resonance, e.g. BIAcore™. To test whether an anti-*P. aeruginosa* LPS antibody cross-competes with another anti-*P. aeruginosa* LPS antibody, one may use the competition method described above in two directions, i.e. determining if the known antibody blocks the test antibody and vice versa.

Antibodies of the invention bind to *P. aeruginosa* LPS with a dissociation constant ($K_d$) of $5 \times 10^{-7}$ M or less, preferably $5 \times 10^{-7}$ M to $1 \times 10^{-7}$ M. In some embodiments, the antibody or antigen-binding portion thereof binds to *P. aeruginosa* LPS with a $K_d$ of $1 \times 10^{-7}$ M to $5 \times 10^{-8}$ M. In some embodiments, the antibody or antigen-binding portion thereof binds to *P. aeruginosa* LPS with a $K_d$ of $5 \times 10^{-8}$ M to $1 \times 10^{-8}$ M. In some embodiments, the antibody or antigen-binding portion thereof binds to *P. aeruginosa* LPS with a $K_d$ of $10^{-8}$ M to $10^{-8}$ M, $10^{-9}$ M to $10^{-10}$ M, or $10^{-10}$ M to $10^{-11}$ M. The binding affinity of an antibody of the invention may be determined by any method known in the art. In some embodiments, the binding affinity is measured by competitive ELISAs or RIAs. In some embodiments, the binding affinity is measured by surface plasmon resonance, such as BIAcore™. In some embodiments, the binding affinity is measured according to the method described in Example XIII of WO 03/040170, published May 15, 2003.

In some embodiments, the antibody has a half-life in vivo of one hour or more. In some embodiments, the antibody or antigen-binding portion thereof has a half-life in vivo of between one hour and thirty days. In some embodiments, the antibody or antigen-binding portion thereof has a half-life in vivo of between sixteen and thirty days. In some embodiments, the antibody or antigen-binding portion thereof has a half-life in vivo of between one hour and fifteen days.

The isolated human antibody or antigen-binding portion thereof that specifically binds to *P. aeruginosa* LPS of the invention may be immunoglobulin G (IgG), IgM, IgE, IgA and IgD. In a preferred embodiment, the IgG may be an IgG1, IgG2, IgG3 or IgG4 subtype. In some preferred embodiments, the IgG is the IgG2 subtype.

In another aspect, the invention provides anti-*P. aeruginosa* antibodies that are labeled. In a preferred embodiment, the label is a radiolabel, an enzyme label, a fluorescent label, a toxin, a magnetic agent, a second antibody, an affinity label, an epitope tag, an antibiotic, a complement protein or a cytokine.

In some embodiments, the antibodies of the invention comprise a kappa or a lambda light chain and framework sequences thereof. In embodiments having a kappa light chain, the framework sequences of the kappa light chain are encoded by a human gene selected from the group consisting of: human Vκ2/A19/A3; human Vκ1/A30; human Vκ4/B3; human Vκ3/A27; human Vκ3/L2; human Vκ1/A30; human Vκ3/L2, L16; and human Vκ1/A30. In some embodiments, the kappa light chain comprises between one and fifteen changes from a kappa light chain encoded by the germline sequence of one of these genes. In some embodiments, the kappa light chain comprises no more than six amino acid changes from a kappa light chain encoded by the germline sequence of one of these genes. In some embodiments, the kappa light chain comprises no more than three amino acid changes from a kappa light chain encoded by the germline sequence of one of these genes.

In some embodiments, the antibody comprises a kappa light chain comprising an amino acid sequence selected from the group consisting of: SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29 and SEQ ID NO: 30. In some embodiments, the antibody comprises a kappa light chain comprising at least one of the FR1, CDR1, FR2, CDR2, FR3, CDR3 and FR4 regions sequence from an amino acid sequence selected from the group consisting of: SEQ ID NO: 22; SEQ ID NO: 23; SEQ ID NO: 24; SEQ ID NO: 25; SEQ ID NO: 26; SEQ ID NO: 27; SEQ ID NO: 28; SEQ ID NO: 29 and SEQ ID NO: 30.

In some embodiments, the variable region of the heavy chain of an antibody of the invention is encoded by a human gene selected from the group consisting of human $V_H3/V4$-04; human $V_H3/V4$-59; human $V_H3/V3$-33; human $V_H3/V3$-15; human $V_H6/V6$-01; and human $V_H5/V5$-51. In some embodiments, the diversity region of the heavy chain is encoded by a human gene selected from the group consisting of human D3-10; human D1-26; human D3-22; human D6-13; and human D6-19. In some embodiments, the joining region of the heavy chain is encoded by a human $J_H3$, human $J_H4$ or human $J_H6$ gene. In some embodiments, the variable region comprises between one and fifteen amino acid changes from a germline human $V_H$ gene sequence. In some embodiments, the heavy chain comprises no more than six amino acid changes. In some embodiments, the heavy chain comprises no more than three amino acid changes.

In some embodiments, the antibody comprises a heavy chain comprising an amino acid sequence selected from the group consisting of: SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; and SEQ ID NO: 21 or the variable domain or CDRs thereof. In some embodiments, the antibody comprises a heavy chain comprising at least one of the FR1, CDR1, FR2, CDR2, FR3, CDR3 and FR4 regions sequence from an amino acid sequence selected from the group consisting of: SEQ ID NO: 13; SEQ ID NO: 14; SEQ ID NO: 15; SEQ ID NO: 16; SEQ ID NO: 17; SEQ ID NO: 18; SEQ ID NO: 19; SEQ ID NO: 20; and SEQ ID NO: 21.

Antigen-binding portions of the anti-*P. aeruginosa* antibodies of the invention include an Fab fragment, an F(ab')₂ fragment or an F$_v$ fragment. In various embodiments, the antibodies of the invention may be chimeric antibodies, bispecific antibodies, single chain antibodies, immunoadhesins, diabodies, mutated antibodies and antibody derivatives.

In some embodiments, the antibody is a single chain antibody.

In some embodiments, the chimeric antibody comprises framework regions and CDR regions from different human antibodies. The chimeric antibody may be bispecific. In some embodiments, the chimeric antibody is bispecific for *P. aeruginosa* LPS and a label selected from the list consisting of a radiolabeled molecule, an enzymatic label, a fluorescent label, a toxin, a magnetic agent, a second antibody, an affinity label, an epitope tag, an antibiotic, a complement protein and a cytokine.

In some embodiments, the anti-*P. aeruginosa* antibody or antigen-binding portion is derivatized. In a preferred embodiment, the antibody or portion thereof is derivatized with polyethylene glycol, at least one methyl or ethyl group or at least one carbohydrate moiety.

In another aspect, the invention provides an isolated human antibody or antigen-binding portion thereof that specifically binds to LPS from one of *P. aeruginosa* strains Fisher Devlin (International Serogroups) It-2 (O11), It-3 (O2), It-4 (O1), It-5 (O10), It-6 (O7), PA01 (O5), 170003 (O2), IATS016 (O2/O5), and 170006 (O2) and a pharmaceutically acceptable carrier. In certain embodiments, the pharmaceutical composition comprises more than one isolated human antibody or antigen-binding portion thereof that specifically binds to *P. aeruginosa* LPS with the same or different binding specificities. In some embodiments, the pharmaceutical composition comprises a plurality of the antibodies of the invention. For example, in some embodiments, the pharmaceutical compositions comprises antibodies specific for two, three, four, five, six, seven, eight or all of *P. aeruginosa* strains Fisher Devlin (International Serogroups) It-2 (O11), It-3 (O2), It-4 (O1), It-5 (O10), It-6 (O7), PA01 (O5), 170003 (O2), IATS016 (O2/O5), and 170006 (O2). The invention further provides a kit comprising one of the aforementioned pharmaceutical compositions and a container. In a preferred embodiment, the kit further comprises instructions for use.

The invention provides a method for treating or preventing *P. aeruginosa* infection, comprising the step of administering an anti-*P. aeruginosa* antibody of the invention or an antigen-binding portion thereof, or a pharmaceutical composition comprising one or more of said antibodies or portions, to a patient at risk of being infected with, or currently infected with, *P. aeruginosa*.

In some embodiments, the human antibody is a monoclonal antibody. In some embodiments, the pharmaceutical composition is administered via an injection, trasmucosal, oral, inhalation, ocular, rectal, long acting implantation, liposomes, emulsion, cream, topical or sustained release means. In another embodiment, the antibody is fused with a second protein. The second protein may be, for example, a toxic peptide moiety, a complement protein, a radiolabeled protein, a cytokine or an antibiotic protein. In some embodiments, the antibody is labeled with a radiolabel, a toxin, a complement protein, a cytokine or an antibiotic. The patient may be any patient having or at risk for *P. aeruginosa* infection as, for example, a burn patient, a surgical patient, a prosthesis recipient, a respiratory patient, a cancer patient, a cystic fibrosis patient or an immunocompromised patient. The pharmaceutical composition may further comprise one or more additional therapeutic or diagnostic agents such as toxins, complement proteins, radiolabeled proteins, cytokines, antibiotics, or any combination thereof.

In some embodiments, the invention provides diagnostic methods in which the antibodies of the invention are used to detect *P. aeruginosa* or LPS in a biological sample in vitro or in vivo. The antibodies can be used in a conventional immunoassay, including, without limitation, an ELISA, an RIA, flow cytometry, tissue immunohistochemistry, Western blot or immunoprecipitation.

The invention provides a method for detecting *P. aeruginosa* or LPS in a biological sample comprising contacting the biological sample with an antibody of the invention and detecting the bound antibody. In some embodiments, the antibody is directly labeled with a detectable label. In some embodiments, the antibody of the invention (the first antibody) is unlabeled and a second antibody or other molecule that can bind the first antibody is labeled. As is well known to one of skill in the art, a second antibody is chosen that is able to specifically bind the particular species and class of the first antibody. For example, if the first antibody is a human IgG, then the secondary antibody could be an anti-human-IgG. Other molecules that can bind to antibodies include, without limitation, Protein A and Protein G, both of which are available commercially, e.g., from Pierce Chemical Co.

Suitable labels for the antibody or secondary antibody include, e.g., various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^{3}H$.

In another aspect, the invention provides an isolated cell line that produces a human antibody or antigen-binding portion thereof that specifically binds to LPS from one of *P. aeruginosa* strains Fisher Devlin (International Serogroups) It-2 (O11), It-3 (O2), It-4 (O1), It-5 (O10), It-6 (O7), PA01 (O5), 170003 (O2), IATS016 (O2/O5), and 170006 (O2). In some embodiments, the cell line is a hybridoma.

The invention further provides a method of producing an isolated human anti-*P. aeruginosa* LPS antibody or antigen-binding portion thereof, comprising the steps of
  a) culturing a non-human cell capable of producing the antibody under conditions in which the antibody is produced;
  b) isolating the antibody from the cell culture.

In some embodiments, the method of producing an antibody of the invention utilizes an immortalized cell, such as a hybridoma. In other embodiments, the method utilizes a cell that is transformed with isolated nucleic acid molecules encoding the heavy chain and/or light chain of the antibody or encoding an antigen-binding portion thereof. Cells suitable for use in the method include bacterial cells, yeast cells, insect cells, amphibian cells and mammalian cells. Those of skill in the art will appreciate that mammalian cells useful in the method include human cells, mouse cells, rat cells, dog cells, monkey cells, goat cells, pig cells, bovine cells and hamster cells. More particularly, useful cells include HeLa cells, NIH 3T3 cells, CHO cells, BHK cells, VERO cells, CV-1 cells, NS/0 cells and COS cells.

In a further aspect, the invention provides a nucleic acid molecule that encodes a heavy chain or a light chain or an antigen-binding portion thereof of an anti-*P. aeruginosa* antibody of the invention. The nucleic acid molecule may be derived from an immortalized cell, such as a hybridoma, that produces the antibody or directly from B cells that produce the antibody.

The invention also provides a vector comprising any of the aforementioned nucleic acids encoding the antibody heavy and light chains or antigen-binding portions. Preferably, the vector further comprises expression control sequences operably linked to the nucleic acid.

The invention further provides an isolated host cell comprising
  a) a nucleic acid molecule that encodes a heavy and/or light chain or an antigen-binding portion thereof of an antibody of the invention; or
  b) a vector comprising the nucleic acid molecule.

As will be appreciated by a skilled worker, the isolated host cells described above may be cells such as hybridoma cells, bacterial cells, yeast cells, insect cells, amphibian cells and mammalian cells. As previously mentioned, the mammalian cells that are useful as host cells include human cells, mouse cells, rat cells, dog cells, monkey cells, goat cells, pig cells, bovine cells and hamster cells. Preferred cells include HeLa cells, NIH 3T3 cells, CHO cells, BHK cells, VERO cells, CV-1 cells, NS/0 cells and COS cells.

The invention also provides an isolated human antibody heavy and/or light chain or antigen-binding portion thereof encoded by any of the nucleic acid molecules described above or isolated from any of the host cells described above. In some embodiments, the isolated human antibody heavy chain or antigen-binding portion thereof comprises between one to ten amino acid substitutions that increase the serum half-life of the antibody.

The invention provides non-human transgenic animals comprising any of the nucleic acid molecules described above. In some embodiments, the animal expresses the nucleic acid molecule or molecules. In some embodiments, the non-human transgenic animal comprises an isolated nucleic acid molecule that encodes a heavy chain or the antigen-binding portion thereof and an isolated nucleic acid molecule that encodes a light chain or the antigen-binding portion thereof of an antibody of the invention and expresses both nucleic acid molecules. The non-human animal may be a mouse, a rat, a hamster, a cow, a sheep, a primate, a horse or a pig. In some embodiments, the antibody or portion thereof is expressed on the surface of cells derived from the animal's B lymphocytic cells or progeny thereof. In some embodiments, the antibody or portion thereof resulting from expression of the isolated nucleic acid molecules is secreted into the lymph, blood, milk, saliva, or ascites of the animal.

The invention provides a fusion protein comprising an antibody of the invention, or antigen-binding portion thereof, and a second polypeptide sequence. The second polypeptide sequence may be an epitope tag, an affinity tag, a toxic polypeptide, an antibiotic, an enzyme, a second antibody sequence, a complement protein, or a cytokine. In some embodiments, the second polypeptide is a diagnostic agent, such as an enzyme that may be easily visualized, such as horseradish peroxidase.

In some embodiments, the heavy chain isotype of an antibody of the invention is mu, gamma, delta, epsilon or alpha.

The invention provides an isolated human antibody or antigen-binding portion thereof isolated from an animal or cell that was free of contaminating human biomaterials. In some embodiments, the biomaterials are viruses, enzymes, hormones, cytokines, receptors, receptor ligands, immunoglobulins, complement, nuclear proteins, and cytoplasmic signaling proteins. In some embodiments, the viruses are Epstein-Barr virus or retroviruses.

Pharmaceutical compositions may be manufactured by means of conventional mixing, dissolving, granulating, dragee-making, levigating, emulsifying, encapsulating, entrapping or lyophilizing processes.

Pharmaceutical compositions for use in accordance with the present invention thus may be formulated in a conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art. For ocular administration, suspensions in an appropriate saline solution are used as is well known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained as a solid excipient, optionally grinding a resulting mixture, and processing the mixture of granules, after adding suitable auxiliaries, if desired, to obtain tablets or dragee cores. Suitable excipients include fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with fillers such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin, for use in an inhaler or insufflator, may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oily such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, such as sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

A pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinyl pyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually with a greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days.

Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The isolated human antibody or antigen-binding portion thereof that specifically binds to *P. aeruginosa* LPS of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

A component of the kits of the present invention comprise instructions for utilizing the compositions of the present invention for prevention or treatment of *P. aeruginosa* infections. Applicant has, for the first time, disclosed herein a method of preventing or treating *P. aeruginosa* infections with an isolated human antibody or antigen-binding portion thereof that specifically binds to LPS from one of *P. aeruginosa* strains Fisher Devlin (International Serogroups) It-2 (011), It-3 (02), It-4 (01), It-5 (010), It-6 (07), PA01 (05), 170003 (02), IATS016 (02/05), and 170006 (02). The printed instructions on the kit enable one of skill in the art to utilize the kit for practicing the methods of the present invention.

Example 1

Generation of Mice and Hybridomas that Produce Fully Human Antibodies to *P. aeruginosa* LPS

*P. aeruginosa* strains Fisher Devlin (International Serogroups) It-1 (06), It-2 (011), It-3 (02), It-4 (01), It-5 (010), It-6 (07), PA01 (05), 170003 (02), IATS016 (02/05), and 170006 (02)—all of which were originally clinical isolates—were used for mouse immunizations, mouse protection assays and opsonic assays. Bacteria for mouse challenge assays were freshly plated onto Pseudosel™ agar (BBL, Becton Dickinson, Sparks, Md.), then were incubated at 37° C., and cells from a single colony were inoculated into LB broth and incubated at 37° C. in a shaking water bath to a concentration of $5\times10^8$ cfu/ml. Bacteria were centrifuged at 10,000 rpm for 10 minutes, resuspended and washed in chilled phosphate buffered saline (PBS) and diluted as needed. Bacteria for immunization experiments were grown as above, heat-killed at 60° C. for one hour and stored at 4° C. until use.

The high molecular weight polysaccharide (high MW PS) portion of the LPS O-specific side chains from *P. aeruginosa* strains Fisher Devlin (International Serogroups) It-1 (06), It-2 (011), It-3 (02), It-4 (01), It-5 (010), It-6 (07), PA01 (05), 170003 (02), IATS016 (02/05), and 170006 (02) were made as described previously, and were lyophilized for storage. See Hatano et al. *Infect. Immun.* 62:3608-3616 (1994). These high MW PS were used to block binding of Mab to bacteria immobilized on microtiter plates for enzyme-linked immunosorbent assays (ELISA) as described in Example 3.

Mice that were transgenic for human heavy and light Ig were bred and maintained by Abgenix Inc., Fremont, Calif. The strain of Xenomouse™ animals used was XMG2, which is an Ig-inactivated mouse reconstituted with a YAC containing cointegrated human heavy and light chain transgenes as previously described. See Mendez et al. *Nature Genet.* 15:146-56 (1997). Mice were housed in micro-isolator cages in a pathogen-free facility after shipping, and food and water were autoclaved prior to use. Mice were immunized with $10^7$ heat-killed *P. aeruginosa* of the various strains intraperitoneally (ip; 10⁷ bacteria in PBS) with Complete Freund's Adjuvant (Sigma, St. Louis Mo.) for the first injection and Incomplete Freund's Adjuvant two weeks later and for the remainder of the four weekly injections. Mouse sera was obtained via tail vein bleed after four to six weeks of immunizations and were screened for anti-O-specific side chain antibodies by ELISA as described below in Example 3. Seropositive mice were boosted by intravenous (iv) injection of 1×10⁷ cfu of heat-killed *P. aeruginosa* bacteria in sterile PBS without any adjuvant four days before splenectomy and fusion were performed.

Hybridomas were generated by fusing spleen and/or lymph node cells from immunized, seropositive Xenomouse™ animals with the nonsecreting sp2/0 myeloma cell line, as described previously. See Mendez et al. *Nature Genet.* 15:146-156 (1997); Schreiber et al. *J. Immunol.* 146:188-193 (1991). Supernatants from hybridomas were screened for production of human anti-*P. aeruginosa* LPS Mabs using the ELISA procedure described below in Example 3. Hybridomas found to be secreting IgG anti-LPS antibodies were then cloned three times by limiting dilution. One IgG2-secreting clone was chosen for each *P. aeruginosa* strain and designated according to the strain against which they were raised as follows: anti-It-2; anti-It-3; anti-It-4; anti-It-5; anti-It-6; anti-PA01; anti-170003; anti-IATS016; and anti-170006.

Example 2

Characterization and Usage of Variable Region Genes from Transgenic Mouse-Derived Anti-LPS Antibody Human heavy-chain and light-chain variable (V) regions were cloned into a T7-promoter driven vector by amplifying the variable regions. The heavy-chain variable ($V_H$) region and the light-chain variable ($V_L$) region primers used are included in Table 1. These primers were synthesized by Integrated DNA Technologies (Coralville, Iowa). PCR was run at 94° C., 60 sec; 50° C., 60 sec; 72° C., 120 sec for 35 cycles. The PCR products were run on a 2% Tris-acetate EDTA agarose gel and the bands (423 bp $V_\kappa$, 441 bp $V_H$) were isolated using the QIAquick® gel-extraction kit (Qiagen, Inc., Valencia, Calif.). The cDNA was cloned into the pT7Blue vector and transformed into *Escherichia coli* using the Perfectly Blunt® Cloning Kit from Novagen (EMD Biosciences, Inc.). Positive clones were grown overnight in LB-ampicillin broth. The DNA was extracted from the bacteria and purified by Qiagen® Miniprep. DNA samples were sent to Cleveland Genomics™ for sequencing. V region sequences were compared and classified using V Base to determine gene usage for each *P. aeruginosa* lipopolysaccharide serotype.

TABLE 1

Primers used to amplify heavy-chain and light-chain V regions.

| Primer | Sequence | SEQ ID NO: |
|---|---|---|
| $V_H3'$ | 5'-CCC AAG CTT TTC GGC GAA GTA GTC CTT GAC CAG GCA GCC CAG-3' | 1 |
| con IgG2 | 5'-GCA CTC ACT AGT ACA TTT GCG CTC AAC-3' | 2 |
| $V_H A$ | 5'-GGG AAT TCA TGG ACT GGA CCT GGA GGR TYC TCT KC-3' | 3 |
| $V_H B$ | 5'-GGG AAT TCA TGG AGY TTG GGC TGA SCT GGS TTT YT-3' | 4 |
| $V_H C$ | 5'-GGG AAT TCA TGR AMM WAC TKT GKW SCW YSC TYC TG-3' | 5 |
| $V_H 1a$ | 5'-GAG GTR CAG YTG CTC GAG TCT GGR G-3' | 6 |
| $V_H 1b$ | 5'-CAG ACK CAG YTG CTC GAG TCT GGG RGC-3' | 7 |
| $V_H 2$ | 5'-CAG GTG CAG CTG CTC GAG TCG GGC-3' | 8 |
| $V_H 3$ | 5'-GAG GTG CAG CTG CTC GAG TCT GG-3' | 9 |
| $V_H 4$ | 5'-CAG GWG CAG CTG CTC GAG TCK GGG-3' | 10 |
| $V_L 3'$ | 5'-CCC AAG CTT CAT CAG ATG GCG GGA AGA-3' | 11 |
| $V_L 1$ | 5'-GGG AAT TCA TGG ACA TGR RRD YCC HVG YKC ASC TT-3' | 12 |

Immunization of the transgenic mice with heat-killed *P. aeruginosa* resulted in the production of IgM and IgG2 human antibodies directed to the LPS O-side chain of the serotype used for immunization, consistent with the constant region reconstitution of this mouse (data not shown). Only IgG2 antibodies were chosen for further characterization. Variable region genes from hybridomas obtained from fusion of spleen cells from *P. aeruginosa*-immunized transgenic mice with the non-secreting sp2/0 cell line were cloned and sequenced in order to determine variable region gene usage. The deduced amino acid sequences of the V regions of the heavy and light chains of these monoclonal antibodies are shown in Tables 2 and 3. The amino acid sequences in Tables 2 and 3 constitute continuous sequences, but are separated by the symbol "—" only to indicate the junctions of the corresponding FR1, CDR1, FR2, CDR2, FR3, CDR3, and J regions, respectively.

TABLE 2

Amino acid sequences of the V regions of the heavy chains.

| Mab | Heavy Chain Sequence | SEQ ID NO: |
|---|---|---|
| Anti-It-2 | QVQLQESGPGLVKPSETLSLTCTVS-GGSISSYYWS-WIRQPAGKGLEWIG-RIYTSGNTNYKPSLKS-RVTMSVDTSKNQFSLKLSSVTAADTAVYYCAR-EVMVRGVTFDY-WGQGTLVTVSSA | 13 |
| Anti-It-3 | QVQLQESGPGLVKPSETLSLTCTVS-GGSVSDYYWS-WIRQPPGKGLEWIG-YIYYSGSTNYNPSLKS-RVTISVDTSKNQFSLKLSSVTAADTAVYYCAR-DGSVPPGIY-WGQGTLVTVSSA | 14 |
| Anti-It-4 | QVQLVESGGGVVQPGRSLRLSCAAS-GFTFRYGMH-WVRQAPGKGLEWVA-VIWYDGNKKYHAESVKG-RFTISRDNSKNTLYLQMNSLRAEDTAVYYCAR-GGFGELPHLYGMDV-WGQGTTVTVSSA | 15 |
| Anti-It-5 | EVQLVESGGGLVKPGGSLRLSCAVS-GFTFSNAWMS-WVRQTPGKGLEWVG-RIKSKTDGGTIDYAAPVKG-RFTISRDDSKNTLYLQMNSLKTEDTAVYYCTK-FYYGSGSYGY-WGQGTLVTVSSA | 16 |
| Anti-It-6 | QVQLQQSGPGLVKPSQTLSLTCAIS-GDSVSSNSAAWN-WIRQSPSRGLEWLG-RTYYRSKWYNDYAVSVKS-RITINPDTSKNQFSLQLNSVTPEDTAVYYCAR-GYYYGMDV-WGQGTTVTVSSA | 17 |
| Anti-170003 | EVQLVESGGGLVKPGGSLRLSCAAS-GFTFSNAWMS-WVRQAPGKGLEWVG-RIKSKTDGGTTDYAAPVKG-RFTISRDDSKNTLYLQMNSLKTEDTAVYYCTT-YYYDSSGYYYY-WGQGTLVTVSSA | 18 |
| Anti-170006 | EVQLVQSGAEVKKPGESLKISCKGF-GYSFASYWIG-WVRQMPGKGLEWMG-NIYPGDSYTIYSPSFQG-QVAISADKSISTAYLQWNSLKASDTAMYYCAR-RGFSGRSYDAFEI-WGQGTMVTVLA | 19 |
| Anti-Pa01 | QVHLQESGPGLVKPSETLSLTCTVS-GGSITNFYWS-WIRQSAGKGLEWIG-RIYISGTTNYNPSLKS-RVTMSLDTSKNQFSLKLSSVTAADTAVYYCAR-GGYSIGWYRDLGSFDI-WGQGTMVTVSSA | 20 |
| Anti-IATS016 | QVQLQESGPGLVKPSESLSLTCTVS-GGSVSSYYWS-WIRQPAGKGLEWIG-LIYTSGSTNYNPSLKS-RVTMSVDTSKNQFSLKLSSVTAADSAVYYCAR-IAAAGTDY-WGQGTLVTVSSA | 21 |

TABLE 3

Amino acid sequences of the V regions of the light chains.

| Mab | Heavy Chain Sequence | SEQ ID NO: |
|---|---|---|
| Anti-It-2 | DIVMTQSPLSLPVTPGEPASISC-RSSQSLLFSNEYNFLD-WFLQKPGQSPQLLIY-LGSNRAS-GVPDRFSGSGSGTDFTLKISRVEAEDVGVYYC-MQALQIPRT-FGQGTKVEIKR | 22 |
| Anti-It-3 | DIQMTQSPSSLSASVGDRVTITC-RASQGIRNVLV-WYQQKPGKAPKRLIY-AASSLQS-GVPSRFSGSGSGTEFTLTISSLQPEDFATYYC-LQHNSYPWT-FGQGTKVEIKR | 23 |
| Anti-It-4 | DIVMTQSPDSLAVSLGERATINC-KSSQNILYNSNNNNYLA-WFQQKPRQPPKLLIY-WASTRES-GVPDRFSGSGSGTDFTLTINSLQAEDVAVYYC-QQYYSAPLT-FGGGTKVEIKR | 24 |
| Anti-It-5 | EIVLTQSPGTLSLSPGERATLSC-RTSQSVSSIYLA-WYQQKPGQAPRLLIY-GASNRAT-GIPDRFSGSGFGTDFTLTISRLEPEDFAVYYC-QQYGRSPLT-FGGGTKVEIKR | 25 |
| Anti-It-6 | ERVMTQSPATLSVSPGERATLSC-RASQSVSSNLA-WYQQKPGQAPRLLIY-GASTRAT-GIPARFSGSGSGTEFTLTISSLQSEDFAVYYC-QQYYHWLT-FGGGTKVEIKR | 26 |
| Anti-170003 | DIQMTQSPSSLSASVGDRVTITC-RASQGIRNDLG-WYQQKPGKAPKRLIY-AASSLQS-GVPSRFSGSGSGTEFTLTISSLQPEDFATYYC-LQYNSYPPT-FGQGTKVEIKR | 27 |
| Anti-170006 | EIVMMQSPGPLSVSPGERAILSCRASQNVNINLA-WYQQKPGQAPRLLIY-GASTRAT-GIPARFSGSGSGTEFTFTISSLQSEDFAVYYC-QQYKNWPLT-FGGGTKVEIKR | 28 |
| Anti-Pa01 | DIVMTQSPDSLAVSLGERATINC-KSSQNILYSSNNKNYLA-WYQQKPGQPPKLLIY-WASTRES-GVPDRFSGSGSGTDFTLTISSLQAEDVAVYFC-QQYYNIRT-FGQGTKVEIKR | 29 |
| Anti-IATS016 | DIQMTQSPSSLSASVGDRVTITC-RASQDIRNDLG-WYQQKPGKAPKRLIY-AASSLQS-GVPSRFSGSGSGTEFTLTISSLQPEDFATYYC-LQYKSYPWT-FGQGTKVEIKR | 30 |

The light-chain gene segments $V_\kappa 2/A2$ and $J_\kappa 1$ were used, as previously reported as commonly used in humans after PS vaccine immunization. See Chung et al. *Infect. Immun.* 63:4219-4233 (1995). However, many other light-chain gene segments were also used as indicated in Table 4. Three of the new protective IgG2 anti-LPS monoclonal antibodies utilized genes from the $V_H 3$ gene family (anti-It-4, It-5 and 170003) but a variety of other V region genes were utilized by other human anti-LPS O-side chain Mab including $V_H 4$, 5 and 6 (Table 4).

TABLE 4

$V_H$ and $V_\kappa$ gene usage by human Mabs against LPS O-side chain of *P. aeruginosa* made in transgenic XenoMouse™ mice.

| *P. aeruginosa* LPS O-Side chain serotype | Mab isotype | $V_H$ region family | $V_\kappa$ region family |
|---|---|---|---|
| O6ad* | IgG2 | $V_H 3/V3-33\ J_H 4$ | $V_\kappa 2/A2\ J_\kappa 1$ |
| It-2 | IgG2 | $V_H 4/V4-04\ J_H 4$ | $V_\kappa 2/A19/A3\ J_\kappa 1$ |
| It-3 | IgG2 | $V_H 4/V4-59\ J_H 4$ | $V_\kappa 1/A30\ J_\kappa 1$ |
| It-4 | IgG2 | $V_H 3/V3-33\ J_H 6$ | $V_\kappa 4/B3\ J_\kappa 4$ |
| It-5 | IgG2 | $V_H 3/V3-15\ J_H 4$ | $V_\kappa 3/A27\ J_\kappa 4$ |
| It-6 | IgG2 | $V_H 6/V6-01\ J_H 6$ | $V_\kappa 3/L2\ J_\kappa 4$ |
| 170003 | IgG2 | $V_H 3/V3-15\ J_H 4$ | $V_\kappa 1/A30\ J_\kappa 1$ |
| 170006 | IgG2 | $V_H 5/V5-51\ J_H 3$ | $V_\kappa 3/L2, L16\ J_\kappa 4$ |
| Pa01 | IgG2 | $V_H 4/V4-04\ J_H 3$ | $V_\kappa 3/A27\ J_\kappa 4$ |
| IATS016 | IgG2 | $V_H 4/V4-04\ J_H 4$ | $V_\kappa 1/A30\ J_\kappa 1$ |

*This antibody was described in WO 02/20619, published Mar. 14, 2002.

Example 3

Detection of Anti-*P. aeruginosa* LPS Antibodies

Enzyme-linked immunosorbent assay (ELISA) was used to detect antibodies to the various serotypes of *P. aeruginosa* LPS O-side chain in sera of immunized mice and in hybridoma supernatants as we have previously described. See Schreiber et al. *J. Immunol.* 146:188-93 (1991). Briefly, 96-well microtiter polystyrene plates (NUNC, Denmark) were coated with 100 µl per well of 2 µg/ml of purified high MW PS or $1\times10^7$ cfu/well heat-killed *P. aeruginosa* overnight at 4° C., washed, and blocked with 200 µl/well of 1% bovine serum albumin (BSA; Sigma-Aldrich, St. Louis, Mo.) in PBS and 0.05% Tween 20™ (Amresco®, Solon, Ohio). Plates were washed and incubated overnight with serial dilutions of Mab or sera in 1% BSA in PBS. Plates were washed, and bound antibodies were detected by adding isotype-specific alkaline phosphatase-conjugated mouse-anti-human polyclonal antibodies (Southern Biotechnology Associates, Birmingham, Ala.). Plates were developed with 100 µl/well of p-nitrophenyl phosphate (PNPP, Sigma-Aldrich) chromogenic substrate in DEA buffer. Optical densities were measured at 415 nm with a microplate reader (Bio-Rad, Hercules, Calif.).

Blocking assays to determine the specificity of Mabs were performed in an identical fashion as above except that soluble *P. aeruginosa* high MW PS or control PS of different concentrations was added to the Mab prior to addition to heat-killed-bacteria-coated 96-well ELISA plates.

The IgG2 human Mabs produced in the transgenic mouse bound to the O-side chain of *P. aeruginosa* of nine different strains. Blocking assays revealed over 90% reduction in binding of the Mab to heat-killed bacteria after preincubation of the Mab with the serogroup-specific purified LPS O-side chain, compared to less than 10% inhibition with the control PS (PS from a non-homologous serotype; FIG. 1). Cross-reaction of Mab, binding with LPS O-side chains from other *P. aeruginosa* strains occurred, but the observed cross-reaction was always serogroup specific (Table 5).

Example 4

Anti-*P. aeruginosa* LPS Antibody Opsonization Promotes Complement-Dependent Phagocytosis The ability of the human monoclonal antibodies to opsonize homologous serotypes of *P. aeruginosa* for uptake by human polymorphonuclear leukocytes (PMN) was measured in a bacterial killing assay as previously described. See Hemachandra et al. *Infect. Immun.* 69:2223-2229 (2001); Schreiber et al. *J. Infect. Dis.* 167: 221-226 (1993); and Schreiber et al. *J. Immunol.* 146:188-193 (1991). Briefly, the killing assay reaction mixture contained 0.1 ml of $1\times10^5$ cfu/ml of live *P. aeruginosa* in RPMI medium with 10% fetal bovine serum (FBS; endotoxin free, GibCo®, Grand Island N.Y.), 0.1 ml of $1\times10^7$ cells/ml of human PMN (obtained from adult volunteers via venipuncture) in RPMI with 10% FBS, 0.1 ml of different concentrations of human Mab to *P. aeruginosa* in RPMI with 10% FBS, 0.1 ml of 1:15 dilution of human serum from an agammaglobulinemic patient in RPMI with 10% FBS. Controls included human IgG2 Mab of a non-homologous serotype, and a reaction mixture in which PMN were omitted, one in which complement was omitted, and one in which antibody was omitted and replaced with RPMI After incubation at 37° C. with shaking at 100 rpm for 90 minutes, bacteria were diluted and then plated for bacterial enumeration.

Figure 2:
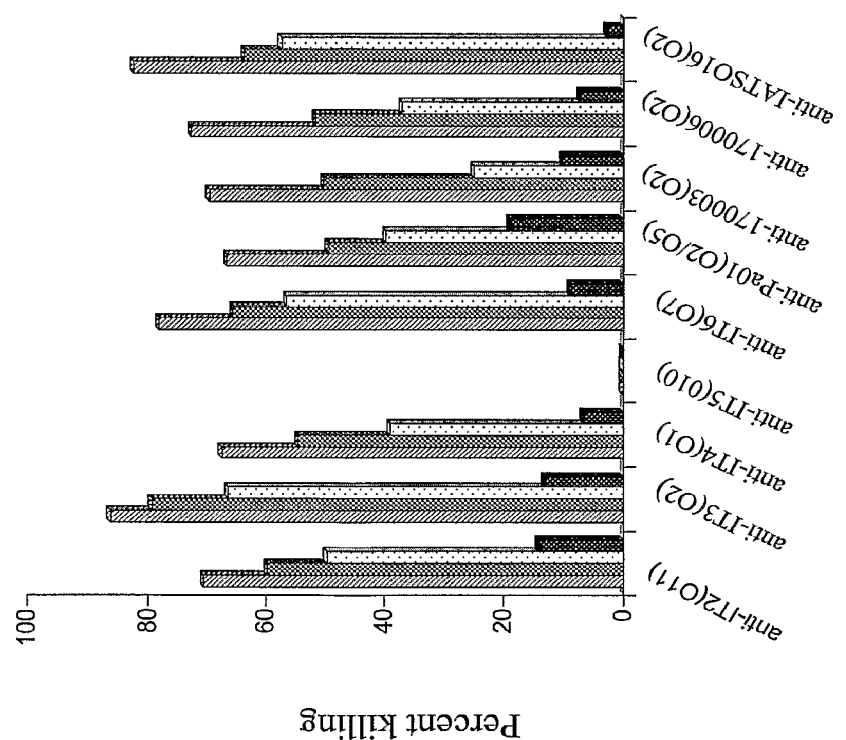
FIG. 2 depicts the results of human complement-mediated killing of *P. aeruginosa* opsonized with serogroup specific human Mabs at various does per ml or irrelevant human Mab.

We tested all nine of the new antibodies for their ability to opsonized homologous strains of *P. aeruginosa* (FIG. 2), Antibody alone was a mediocre opsonin conforming to our previous findings that Fcγ receptor stimulation without complement receptor stimulation is not optimal for phagocytosis of *P. aeruginosa* by human PMN. See Berger et al. *Pediatr. Res.* 35:68-77 (1994). Complement alone yielded some increased uptake of labeled bacteria by PMN, but the phagocytosis was greatly enhanced with antibody and complement together, as predicted when both Fcγ and complement receptors are stimulated together in human PMN (data not shown; Berger et al. supra). Interestingly, one Mab against It-5 *P. aeruginosa* was non-opsonic in this assay despite specific binding to It-5 bacteria and inhibition of this binding by purified LPS O-side chain. This antibody, however, was protective against fatal sepsis with It-5 bacteria (see below).

TABLE 5

Specificity of human Mabs against *P. aeruginosa* serogroups.

| Serotype of *P. aeruginosa* | Anti-It-1 (O6)* | Anti-It-2 (O11) | Anti-It-3 (O2) | Anti-It-4 (O1) | Anti-It-5 (O10) | Anti-It-6 (O7) | Anti-Pao-1 (O2/O5) | Anti-170003 (O2) | Anti-170006 (O2) | Anti-IATSO-16 (O2) |
|---|---|---|---|---|---|---|---|---|---|---|
| It-1 (O6) | +++ | — | — | — | — | — | — | — | — | — |
| It-2 (O11) | — | +++ | — | — | — | — | — | — | — | — |
| It-3 (O2) | — | — | +++ | — | — | — | — | — | — | +++ |
| It-4 (O1) | — | — | — | +++ | — | — | — | — | — | — |
| It-5 (O10) | — | — | — | — | +++ | — | — | — | — | — |
| It-6 (O7) | — | — | — | — | — | +++ | — | — | — | — |
| It-7 (O2) | — | — | — | — | — | — | +++ | — | +++ | — |
| Pao-1 (O2/O5) | — | — | — | — | — | — | +++ | — | — | — |
| 170003 (O2) | — | — | — | — | — | — | — | +++ | — | — |
| 170006 (O2) | — | — | — | — | — | — | — | — | +++ | — |
| 170007 (O2) | — | — | — | — | — | — | — | — | +++ | — |
| IATSO-16 (O2) | — | — | +++ | — | — | — | — | — | — | +++ |
| O6ab | — | — | — | — | — | — | — | — | — | — |
| O6ac | — | — | — | — | — | — | — | — | — | — |
| O6ad | +++ | — | — | — | — | — | — | — | — | — |

*This antibody was described in WO 02/20619, published Mar. 14, 2002.

Example 5

Protection of Neutropenic Mice from Fatal *P. aeruginosa* Sepsis

In order to determine whether the in vitro specificity and opsonic ability of the monoclonal antibodies translated to in vivo protective efficacy, the protective efficacy of the human Mab against sepsis caused by homologous serotypes of *P. aeruginosa* was measured in the neutropenic mouse model as we have described previously. See Pier et al. *Infect. Immun.* 57:174-179 (1989) and Schreiber et al. *J. Immunol.* 146:188-193 (1991). Female, six week-old BALB/c ByJ mice (Jackson Laboratories, Bar Harbor, Me.) were maintained in a pathogen-free, pseudomonas-free environment in which water, bedding, and food were autoclaved prior to use. Neutropenia was established by administering 3 mg of cyclophosphamide (Cytoxan®, Bristol-Myers Squibb, Princeton, N.J.) intraperitoneally (ip) to each mouse on days 1, 3, and 5. On day 5, the cyclophosphamide was administered at time 0 hours, and 2 hours later 25 or 50 mg of antibody was administered ip, followed by $10^3$ cfu of live *P. aeruginosa* two hours later. Negative control mice received PBS ip since we had previously shown that control mice receiving irrelevant Mab or saline in this model had the same death rates. See Hemachandra et al. *Infect. Immun.* 69:2223-2229 (2001). Mice were observed daily thereafter for 7 days since all mortality uniformly occurred prior to this endpoint. Cumulative mortality was the outcome measured, but mice that were unable to move were euthanized prior to the 7-day end point since observation indicated that 100% of these mice subsequently died. 5 mice were used for each group.

Figure 3:
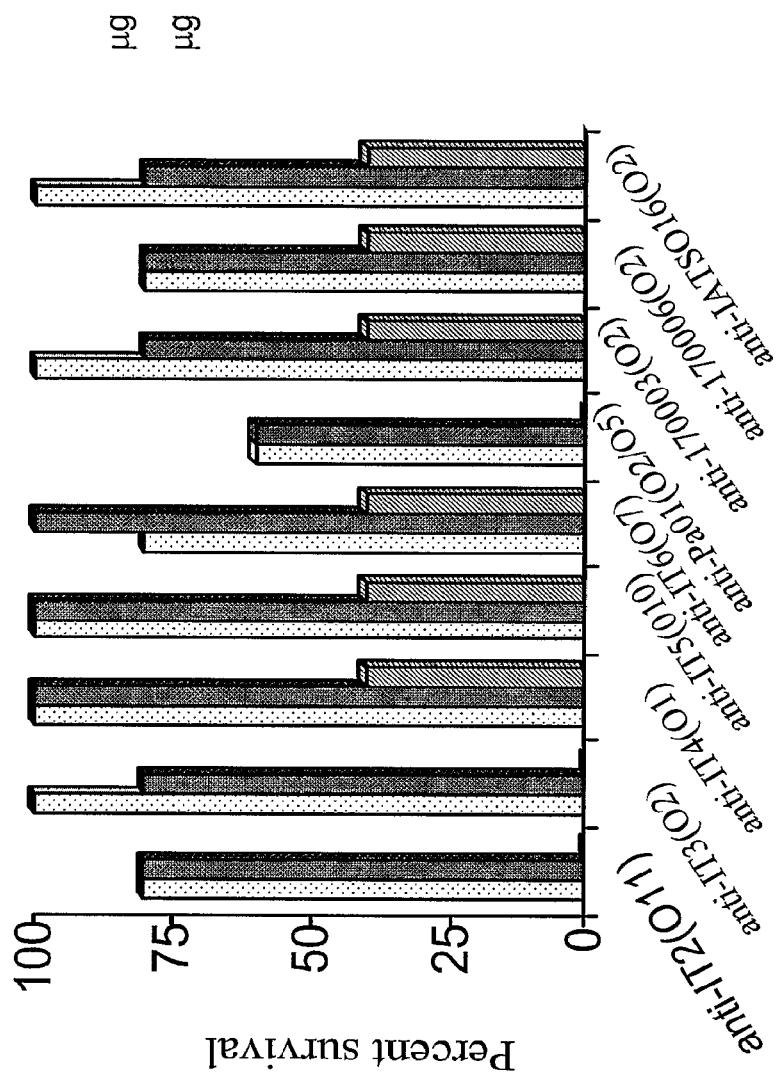
FIG. 3 shows data from a protection experiment in neutropenic mice. The x-axis represents the serotype of the challenge strain of *P. aeruginosa* and the y-axis represents percent survival seven days after challenge.

Mice receiving saline injection and then challenged with *P. aeruginosa* sustained high mortality, most dying within 48 hours after challenge, consistent with previous descriptions of mortality in non-immune mice in this model. In contrast, those mice receiving the human Mabs derived from the XenoMouse™ animals were strongly protected from mortality (FIG. 3).

Throughout this specification and claims, the word "comprise," or variations such as "comprises" or "comprising" will be understood to imply the inclusion of a stated integer or group of integers but not the exclusion of any other integer or group of integers.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Biological Deposits

Hybridoma cell lines producing Mabs that recognize the LPS of strains Pa01, It-5, and It-6 were deposited in accordance with the provisions of the Budapest Treaty at the American Type Culture Collection (ATCC®), 10801 University Blvd., Manassas, Va. 20110-2209, USA on Aug. 6, 2003. They were assigned the following deposit designations and accession numbers:

| | |
|---|---|
| αPa01 IgG2 Hybridoma | PTA-5384 |
| αIt-5 IgG2 Hybridoma | PTA-5385 |
| αIt-6 IgG2 Hybridoma | PTA-5386 |

A hybridoma cell line producing Mabs that recognize the LPS of strain It-2 was deposited in accordance with the provisions of the Budapest Treaty at the American Type Culture Collection (ATCC®), 10801 University Blvd., Manassas, Va. 20110-2209, USA on May 17, 2012. It was assigned deposit designation PTA-12910.

What is claimed is:

1. A hybridoma cell line having American Type Culture Collection Deposit Designation PTA-12910.

2. A monoclonal antibody produced by the hybridoma cell line according to claim 1.

* * * * *